US008920388B2

(12) United States Patent
Slocum et al.

(10) Patent No.: US 8,920,388 B2
(45) Date of Patent: Dec. 30, 2014

(54) METHODS AND DEVICES FOR SENSING TISSUES AND TISSUE COMPARTMENTS

(75) Inventors: Alexander Slocum, Bow, NH (US); Erik Bassett, Cambridge, MA (US); Jeffrey M. Karp, Brookline, MA (US); Robert S. Langer, Newton, MA (US); Omid C. Farokhzad, Chestnut Hill, MA (US)

(73) Assignees: Massachusetts Institute of Technology, Cambridge, MA (US); The Brigham and Women's Hospital, Inc., Boston, MA (US)

( * ) Notice: Subject to any disclaimer, the term of this patent is extended or adjusted under 35 U.S.C. 154(b) by 1342 days.

(21) Appl. No.: 12/525,931

(22) PCT Filed: Feb. 7, 2008

(86) PCT No.: PCT/US2008/001622
§ 371 (c)(1),
(2), (4) Date: Jan. 31, 2011

(87) PCT Pub. No.: WO2008/097609
PCT Pub. Date: Aug. 14, 2008

(65) Prior Publication Data
US 2011/0125107 A1    May 26, 2011

Related U.S. Application Data

(60) Provisional application No. 60/899,920, filed on Feb. 7, 2007.

(51) Int. Cl.
*A61M 5/32*    (2006.01)
*A61B 17/34*   (2006.01)
*A61B 19/00*   (2006.01)

(52) U.S. Cl.
CPC ....... *A61B 17/3401* (2013.01); *A61B 2019/464* (2013.01)
USPC .......................................... 604/272

(58) Field of Classification Search
CPC ................. A61B 17/3401; A61B 2019/464; A61B 17/3417
USPC .................. 604/272, 273, 274, 506, 117
See application file for complete search history.

(56) References Cited

U.S. PATENT DOCUMENTS 4,414,983 A * 11/1983 Evans et al. .................. 600/560
4,940,458 A *  7/1990 Cohn .......................... 604/512

(Continued)

FOREIGN PATENT DOCUMENTS

WO    WO 2002/056937 A2    7/2002

*Primary Examiner* — Emily Schmidt
*Assistant Examiner* — Michael J Anderson
(74) *Attorney, Agent, or Firm* — Wolf, Greenfield & Sacks, P.C.

(57) ABSTRACT

An apparatus provides feedback regarding the material in which tip of the apparatus is located as the tip is advance into matter of varying resistances. The apparatus responds to a change in pressure, force, or other parameter such that when the tip reaches matter of a certain resistance, a change in the parameter is sensed. The apparatus provides a driving force to a penetrating medical device, such as a needle, when the apparatus tip encounters material of high resistance. When the apparatus tip encounters a low resistance material, no further driving force is applied to the apparatus. An inner core may be advanced into the low resistance material for deployment of a gas or a liquid as desired.

13 Claims, 17 Drawing Sheets

(56) References Cited

U.S. PATENT DOCUMENTS

| | | | | |
|---|---|---|---|---|
| 4,983,166 A | | 1/1991 | Yamawaki | |
| 5,232,442 A | * | 8/1993 | Johnson et al. | 604/506 |
| 5,300,084 A | * | 4/1994 | Johnson | 606/185 |
| 5,334,159 A | * | 8/1994 | Turkel | 604/158 |
| 5,517,846 A | * | 5/1996 | Caggiani | 73/1.58 |
| 5,685,852 A | * | 11/1997 | Turkel et al. | 604/159 |
| 5,797,906 A | * | 8/1998 | Rhum et al. | 606/48 |
| 5,836,914 A | * | 11/1998 | Houghton | 604/117 |
| 6,001,084 A | * | 12/1999 | Riek et al. | 604/272 |
| 6,190,370 B1 | * | 2/2001 | Tsui | 604/508 |
| 6,512,958 B1 | * | 1/2003 | Swoyer et al. | 607/117 |
| 2006/0173480 A1 | * | 8/2006 | Zhang | 606/185 |
| 2007/0142766 A1 | * | 6/2007 | Sundar et al. | 604/66 |
| 2007/0244446 A1 | * | 10/2007 | Sundar et al. | 604/218 |
| 2008/0249467 A1 | * | 10/2008 | Burnett et al. | 604/117 |
| 2009/0131825 A1 | | 5/2009 | Burbank et al. | |

\* cited by examiner

METHODS AND DEVICES FOR SENSING TISSUES AND TISSUE COMPARTMENTS

CROSS-REFERENCE TO RELATED APPLICATIONS

This application is a national stage filing under 35 U.S.C. § 371 of international application PCT/US2008/001622, filed Feb. 7, 2008, which claims the benefit under 35 U.S.C. § 119(e) of U.S. provisional application serial number 60/899,920, filed Feb. 7, 2007.

FIELD

The inventions disclosed herein relate generally to penetrating medical devices, and more particularly to penetrating medical devices, such as needles, that are to be placed into specific tissues or regions of various tissues or tissue compartments.

STATEMENT REGARDING FEDERALLY FUNDED RESEARCH

No federal funds were used in the development of the invention.

DISCUSSION OF RELATED ART

Various medical procedures employ the placement of needles or other penetrating medical devices within the body. Because direct visual observation of the position of the devices within the body is not possible in many procedures, placement of the devices can be challenging. Examples of medical procedures in which placement of the tip of a penetrating device is important include:

Arterial Cannulation

Arterial Cannulation (A-lines) is a common procedure in surgery and intensive care to allow arterial pressure monitoring, repeated blood gas sampling, and access to blood for other quantitative assays. Typically, A-lines are inserted in the radial artery of the wrist, but also may be inserted into the axillary artery in the underarm, the femoral artery in the groin, and the pedal artery in the foot. Over eight million A-lines are placed each year in the USA and over 2.5 million are placed in Europe each year. Recently, a 2004 guest editorial in the Journal of Critical Care commented that "even such a frequently used and seemingly benign procedure as cannulation of the radial artery can result in serious complications. The possibility of complications is especially high in critically ill patients who have other co-morbid conditions." Significant complications such as arterial thrombosis, infection, hematoma, nerve injury, and ischemia leading to necrosis of tissues are estimated to range from 15% to 40% and the risk increases with multiple puncture attempts which are often required. In fact, approximately 20% of procedures result in temporary occlusion of the artery requiring an additional puncture event. The increase in risk with multiple punctures is due to direct trauma and increased risk of vasospasm. Multiple punctures also increase the time of the procedure which is typically performed under emergent conditions and thus can compromise stability and life of the patient. Additional attempts typically may be required in as many as 65% of procedures. Inability on the part of the clinician to pass the wire or catheter through the artery is one of the most common difficulties in catheterization. This can occur despite the return of pulsatile blood due to the angle of the needle in relation to the vessel. That is, the angle may be too acute or because the tip is not completely placed within the artery.

Central Venous Catheterization

Central venous catheterization (CVC), or central line placement, involves the cannulation of a vein with a relatively large bore catheter. Central lines are inserted into patients needing access for large amount of fluid administration; those needing monitoring of the central venous pressure; or patients on long-term intravenous therapies for administration of nutrition or medications (i.e., fluids, blood and derivatives, drugs, parenteral nutrition). The most common sites of insertion are the internal jugular vein (neck), subclavian vein (chest), or femoral vein (groin). Central line placement is generally performed by identifying external anatomical landmarks. However, typical anatomical variation of veins is approximately 8% and can be as high as 36% in cancer patients which can complicate CVC. Furthermore, the complication rate may correlate with the physician's level of experience. Therefore, it is not surprising that this procedure is associated with complications such as pneumothorax, inadvertent arterial central line placement, nerve injury, and hematoma in reportedly 14% of patients during emergent procedures.

Aside from requiring multiple needle insertions, occasionally arteries are incorrectly identified as veins and this misidentification is associated with a high incidence of related complications. Specifically, inadvertent placement of a central line into an artery instead of a vein is a prominent cause of morbidity and mortality and may occur in as many as 4.2% of cannulation procedures.

FIG. 1 shows a central line catheter 100 being tunneled under the skin and advanced through the subclavian vein 102 into the right side of the heart.

Epidural Placement

The current state of the art in epidural anesthesia involves the use of an epidural needle (such as a typical Tuohy needle 200) containing a stylet 202 with a blunt end 204, as shown in FIG. 2. The operator performs a blind pass of needle 200 through several tissue layers listed here in order of penetration, some of which are shown in FIG. 3: 1) skin 206, 2) subcutaneous tissue (not shown), 3) supraspinous ligament (not shown), 4) intraspinous ligament 212, and 5) ligamentum flavum 214 to enter the epidural space 215.

Tuohy needle 200 includes a hollow needle that is slightly curved at the distal end 220. During epidural placement, stylet 202, which includes a solid rod with a blunt end, is inserted into the Tuohy needle to prevent tissue from clogging the barrel of the needle. After the needle reaches the epidural space, the stylet is removed and a catheter 222 is inserted into the epidural space via the epidural needle. The curved end of the needle ensures that they catheter is inserted superiorly to the needle within the epidural space. The properly positioned catheter is connected to a syringe 224 for injection of anesthetic agent.

To guide proper placement, the operator uses anatomical landmarks identified by palpation together with changes in the force required to insert the needle through various layers of tissue. Consequently, successful epidural catheter placement requires a high degree of clinical skill on the part of the operator. To ensure proper placement of the needle tip, the operator delicately navigates the needle through the local anatomy, and substantially relies on manual haptic feedback to avoid puncturing the dura 216 and the spinal cord 218 which lies deep to the dura 216. Extreme caution is therefore exercised in the positioning of the needle tip within the narrow epidural space (see epidural space 215 in FIG. 3). To complicate matters, the epidural space has an irregular configuration and therefore the depth of needle penetration depends on the needle trajectory. In addition, during pregnancy and in morbidly obese patients, the anatomical landmarks are typically largely obscured. Attempts to correlate skin-to-epidural space distance with patient variables such as body-to-mass index have not proven useful and thus identification of the epidural space remains a technically demanding procedure, especially given that the skin-to-epidural space distance varies between 20-90 mm. If the needle is inserted too far resulting in the puncture of the dura matter and reaching the subarachnoid space, which occurs in approximately 3% of placement attempts (representing an incidence of 72,000 per year in the U.S. alone), a loss of cerebrospinal fluid (CSF) may ensue leading to disabling complications such as Post-dural Puncture Headache (PDPH) in 50% of these patients. If this misplacement is undetected and the falsely placed epidural catheter is utilized, the anesthesia in the subarachnoid space may reach high enough levels to cause spinal blockade and/or severe motor blockade, which may ultimately result in a rare but devastating complication of respiratory arrest hemodynamic shock.

SUMMARY OF THE INVENTION

Various embodiments disclosed herein may be used for one or more types of medical procedures, including, but not limited to: arterial cannulation; central venous catheterization; general catheter placement; administration of epidurals; placement of chest tubes; peritoneal punctures; Nucleoplasty®; percutaneous access to the brain; and laparoscopy. Various embodiments disclosed herein may be particularly useful when performing procedures on obese patients. As only one example, embodiments disclosed herein may be helpful in preventing complications associated with performing laparoscopy on obese patients. Initial needle placement for insufflation of gas into the peritoneal cavity can puncture organs due to the difficulty of sensing entry into the peritoneal cavity.

Various embodiments disclosed herein may be used as part of other procedures, including, but not limited to: detection of cavities, low density tissue, or a fluid-filled cavity within a body; removal of fluid, tissue, an implanted device, or air; addition of fluid, graft tissue, a device, or air; delivery of adhesives, sutures, staples, graft material, or graft substitute; and detection of cancerous tissue or borders of cancerous tissue. Such procedures may be performed as part of human or veterinarian procedures.

Placement of a penetrating medical device during a medical procedure is achieved by incorporating a component into a lumen of the medical device that responds to pressure encountered at the tip of the device. The component may be used to sense position and/or as part of a system of controlling advancement of the medical device.

According to one aspect of embodiments of the invention disclosed herein, an apparatus is provided that can provide information regarding the resistance of the material in which the tip of the apparatus is located. As the tip is advanced through structures of varying resistances this information may be used to determine the position of the tip relative to those structures. The apparatus provides a response to changes in pressure, force, or other parameter such that when the tip reaches matter of a certain resistance, the apparatus responds. The response may be used to indicate, such as to a human operator or a machine controller, the position of the tip. The response may alternatively or additionally be used to control application of a driving force to the apparatus, such as to remove the driving force when the tip is positioned in a structure of a desired resistance.

In one embodiment, a membrane or other flexible element may be provided at the penetrating (distal) tip of the needle and configured such that upon advancement of the needle into a low resistance matter, the membrane at the distal tip of the needle expands, inflates, or otherwise responds to a decrease in resistance. That response may be communicated to the proximal end of the needle or other location where it may be observed or used to control driving force on the apparatus. Change in resistance at the tip may be communicated in any of multiple ways, including by sensing a displacement of fluid from the proximal end to the distal end as the membrane, upon encountering lower resistance, expands. Such a needle may be used in medical procedures in which a needle tip (or other penetrating medical device tip) is to be placed in a bodily lumen, cavity, or other region of material providing low resistance such that a drop in pressure indicates that no further driving of the needle should occur.

In other embodiments, the sensed resistance at the tip of the penetrating device may be used to selectively couple a driving force to the penetrating device. For example, a driving force may be coupled to a penetrating medical device, such as a needle, when the apparatus tip encounters material of high resistance. When the tip encounters a low resistance material, no further driving force is applied to the penetrating medical device. For purposes herein, areas of low resistance include cavities containing little or no solid matter. Such a penetrating medical device may be implemented, in some embodiments, with a needle including a force-providing element and a clutch which selectively engages and disengages the penetrating medical device from the force-providing element depending on the resistance of the matter through which the needle is being advanced.

In other embodiments, a membrane or other expanding element may be provided at the penetrating (distal) tip of the needle, and configured such that upon advancement of the needle into a low resistance matter, the membrane inflates and retards further needle advancement.

In one embodiment, a device that is adapted to penetrate a body includes at least one first member having a distal tip and a lumen having an opening adjacent the distal tip. The device also includes a second member disposed within the lumen, the second member having a structural surface exposed through the opening, and the second member being adapted to have a first state in response to a first pressure on the surface and a second state in response to a second pressure on the surface.

In another embodiment, a method of operating a device that is adapted to penetrate a body is provided. The device includes at least one first member having a distal tip and a lumen having an opening adjacent the distal tip, and a second member disposed within the lumen. The second member has a surface exposed through the opening. The method includes advancing the device through a first region of the body, the first region providing a first resistance to penetration of the device, whereby the second member has a first configuration in response to a first pressure on the surface created by the first resistance. The method further includes advancing the device into a second region of the body, the second region providing a second resistance to penetration of the device, whereby the second member has a second configuration in response to the second pressure on the surface created by the first resistance.

In a further embodiment, a method of sensing the region of a body in which a section of a penetrating medical device is positioned is provided. The section of the penetrating medical device has a structural surface that is coupled to a fluid held within the penetrating medical device by the structural surface. The method includes inserting the section of the penetrating medical device into the body, and with the section of the penetrating medical device positioned in a first region of the body, sensing a first pressure on the structural surface. With the section of the penetrating medical device positioned in a second region of the body, the method also includes sensing a second pressure on the structural surface.

In another embodiment, an apparatus includes a penetrating medical device having a distal tip, and a movable membrane positioned near the distal tip and coupled to a fluid held within the penetrating medical device by the movable membrane.

In a further embodiment, a method of positioning a penetrating medical device within a body is provided. The device includes a first element having a distal tip and a second element having a distal surface adjacent the distal tip. The method includes inserting the distal tip into the body with the surface in contact with the body. The method further includes exerting a force on the second element, the force deforming the second element when the distal tip of the penetrating medical device is positioned in a first region having a first resistance to advancement such that the second element engages the first element and transfers at least a portion of the force to the first element, whereby a driving force is applied to the first element which advances the penetrating medical device through the body.

In another embodiment, a method of positioning a penetrating medical device within a body is provided. The device includes a first element having a distal tip, and a second element within the first element, the second element having a distal surface adjacent the distal tip. The method includes inserting the distal tip into the body, exerting a force on the second element, and with the distal tip positioned in a first matter having a first resistance to advancement of the penetrating medical device through the body, advancing the penetrating medical device through the first matter. Upon the distal tip reaching a second matter having a second resistance that is lower than the first resistance, exertion of the same force on the second element increases the surface area of the penetrating medical device that is exposed to the body, thereby resisting advancement of the penetrating medical device.

In a further embodiment, a medical device that is adapted to penetrate a body includes a first element having a distal tip and a lumen having an opening, and a force-providing element disposed in the lumen. The force-providing element is configured to receive an applied force and selectively transfer at least a portion of the applied force to the first element based at least in part on the resistance of the matter which the force-providing element contacts at the opening.

In another embodiment, a device that is adapted to penetrate an object includes a first element configured to have at least a portion advanced into an object, the first element having a channel, and the channel having an opening. The device further includes a force-providing element which is configured to receive an applied force and selectively transfer at least a portion of the applied force to the first element via contact between the force-providing element and an internal surface of the channel. When the force-providing element encounters a first resistance to advancement through the object, the force-providing element has first shape such that sufficient contact exists between the force-providing element and the internal surface of the channel to transmit force from the force-providing element to the first element. When the force-providing element encounters a second resistance to advancement through the object, the second resistance being lower than the first resistance, the force-providing element has a second shape such that insufficient contact exists between the force-providing element and the internal surface of the channel to substantially advance the first element through the object via transmission of force from the force-providing element to the internal surface of the channel.

All aspects of the invention need not be present in various embodiments of the invention, and one embodiment may instantiate multiple aspects. Various combinations of aspects and features disclosed herein may be present in embodiments of the invention. Additionally, while certain advantages and features of embodiments are described herein, a device, apparatus, system or method need not necessarily provide every advantage or include every feature to fall within the scope of the invention.

DETAILED DESCRIPTION

Figure 1:
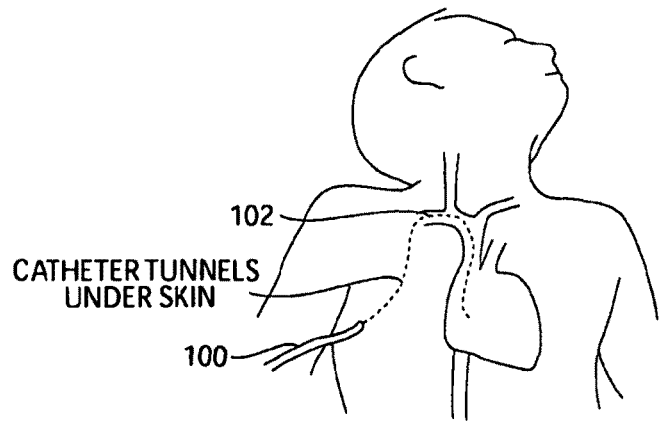
FIG. 1 shows a prior art method of central venous catheter placement within the subclavian vein and into the right side of the heart.
Figure 2:
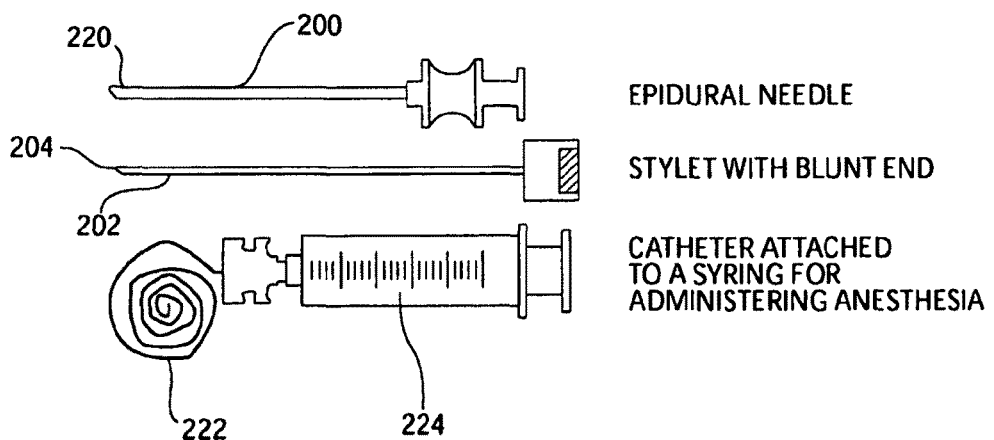
FIG. 2 shows a prior art Tuohy needle and associated components.
Figure 3:
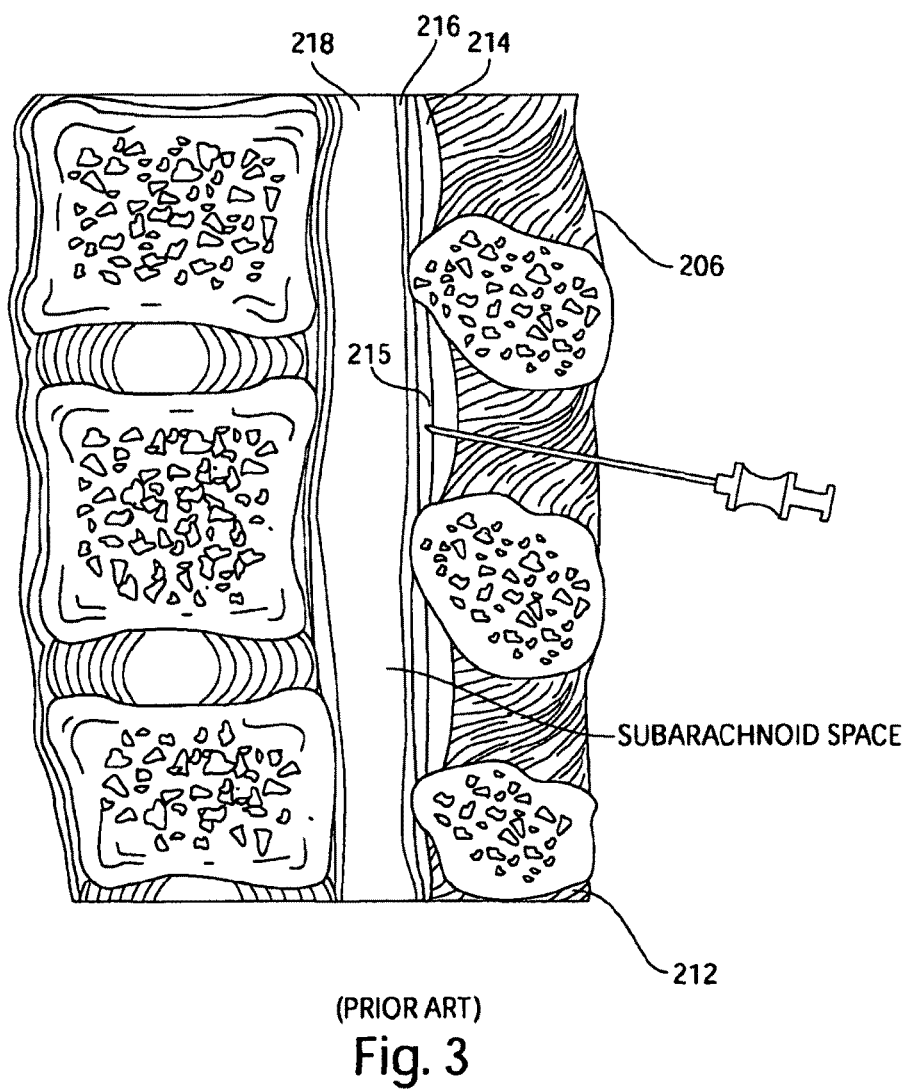
FIG. 3 shows a prior art Tuohy needle being advanced into the epidural space.
Figure 4:
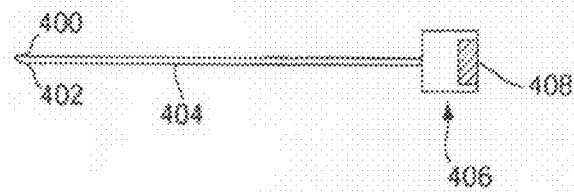
FIG. 4 shows a stylet according to one embodiment of the invention.
Figure 5A:
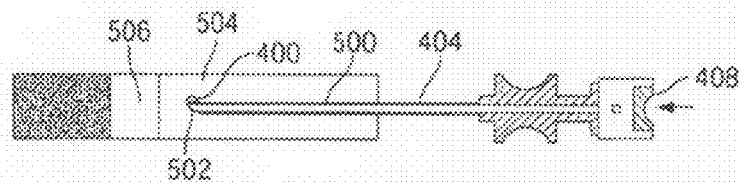
FIGS. 5b and 5b illustrate the advancement of a needle from a high resistance matter into a low resistance matter according to one embodiment of the invention.
Figure 5B:
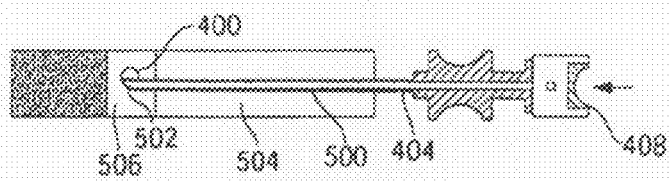

One example of a penetrating medical device that may be used in embodiments of the invention is a stylet. In one embodiment, as shown in FIG. 4, an inflatable, elastic membrane 400 is housed in a distal end 402 of a hollow stylet 404 containing a fluid (e.g., saline). As illustrated in FIGS. 5a and 5b, stylet 404 is held within a needle 500 as both elements are advanced through tissue. A proximal end 406 of the stylet may include a second membrane 408 that is in communication with membrane 400 as a result of the fluid between them. Exertion of force on one membrane tends to displace the other membrane.

In the embodiment illustrated, membrane 408 is configured and positioned similarly to a plunger at the end of a syringe. Such a configuration allows a human operator to exert a force on membrane 408 and to sense the amount of force needed to be applied to membrane 408 to displace membrane 400.

In the embodiment illustrated, membrane 400 is displaced by inflating and the amount of force needed to inflate distal membrane 400 depends on the resistance of the material in which membrane 400 is positioned. The operator detects the penetration of the stylet 404 (and hence a needle tip 502) into certain tissues or tissue compartments by haptically sensing changes in resistance while exerting pressure on distal membrane 408. In the embodiment illustrated, an operator may sense a change in resistance because inflation of membrane 400 causes a displacement of fluid from the proximal end to the distal end, with a corresponding motion of membrane 408.

For example, as shown in FIGS. 5a and 5b, the amount of force required to inflate membrane 400 may be used to determine when the tip 502 of the needle exits high resistance matter 504 and enters a tissue compartment, such as an epidural space 506. When needle tip 502 reaches the epidural space 506, membrane 400 expands because of the pressure being applied to membrane 408 creating a pressure on membrane 400 greater than that generated by the low resistance of epidural space 506. An operator may haptically sense the pressure change by maintaining contact with membrane 408. Though any suitable mechanism may be used to sense the change in pressure, including, in some embodiments, a pressure sensor (not shown) which may be coupled to the stylet to sense when a sudden pressure drop occurs, and thus indicate that the epidural space has been reached by tip 502.

For purposes herein, membrane 400 is considered to be a member having a structural surface. In a needle having a distal tip with fluid directly exposed through an opening in the distal tip, the fluid is not considered to have a structural surface exposed through the opening, although the fluid is still considered to be a member. Any suitable material may be used to form membrane 400. Membrane 400 may be degradable or non-degradable depending on the desired uses of the apparatus and/or the desire characteristics of the apparatus. In some embodiments, membrane 400 and/or membrane 408 may be housed within a needle instead of within a stylet within a needle. Also, a penetrating medical device other than a needle may be used. For example, a trocar or an apparatus without a sharp tip may be used in conjunction with one or more membranes or other embodiments described herein.

As needle 500 is being advanced, to prevent membrane 400 from being pushed into the barrel of the stylet, stylet tip 402 may include a protective element (not shown) between membrane 408 and the interior of the stylet. The protective element may be, for example, a meshwork or a fenestrated surface made from synthetic or natural materials which are degradable or non-degradable materials or combinations thereof. In some embodiments, the apparatus may contain a mechanism that prevents the membrane from remaining inflated during withdrawal of the needle.

Detection of a dural puncture with prior art epidural needles can be made by observing fluid leakage from the body into the syringe. To permit a similar method of detecting a dural puncture with embodiments disclosed herein, a channel or other longitudinal space may be provided between stylet 404 and interior walls of needle 500. This channel allows fluid leakage toward the proximal end of the needle so that the operator can observe fluid leakage.

Currently used epidural placement methods include removing the stylet from the needle and inserting a syringe filled with air or saline to check for loss of resistance to the injection of air or saline. Sometimes, multiple exchanges of the stylet and the syringe are required. Additionally, in some instances, undesirable amounts of air or saline may be injected into the body. Through the use of various embodiments disclosed herein, an operator may detect entry of the needle tip into specific tissue or tissue compartment without the associated complications of injecting air or saline into the body. By not repeatedly exchanging a syringe and a stylet, a more rapid detection of the epidural space also may be achieved by using embodiments described herein. In addition, opening an inflatable membrane into the epidural space may facilitate passage of a catheter for administration of anesthesia.

An apparatus similar to the one illustrated in FIGS. 5a and 5b may be used to perform central line placement. When performing central line placement, the operator is able to detect entry into a vein or artery based on relative differences in pressure. Thus, embodiments disclosed herein may be used to quickly assess entry of the needle into various levels of tissue or tissue compartments. By helping to indicate false arterial cannulization, the apparatus provides the operator with time to reposition the needle prior to insertion of large bore catheters, which is the step that results in most of the complications of CVC discussed above. In some embodiments, the apparatus may be configured to attach to currently existing needles and/or syringes.

Figure 6A:
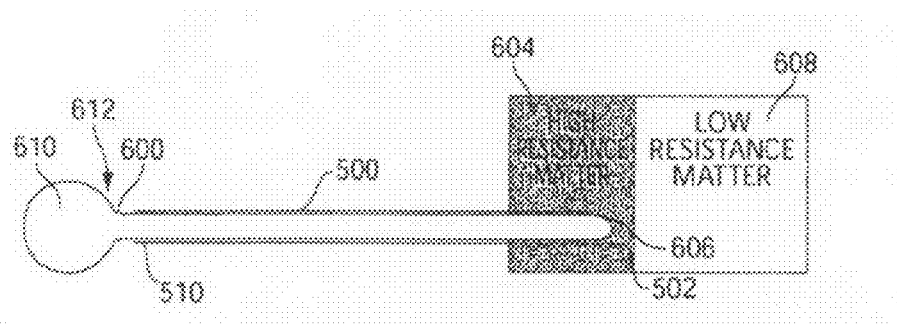
FIGS. 6a and 6b illustrate a continuous balloon within a penetrating medical device according to another embodiment of the invention.
Figure 6B:
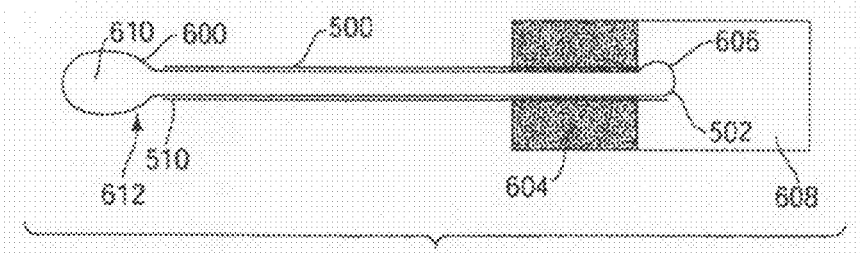

In the embodiment of FIG. 4 and FIGS. 5a and 5b, a proximal and a distal membrane are in communication such that resistance encountered at the distal surface is communicated to the proximal membrane for sensing. As described, fluid within a stylet provides communication between the proximal and distal surfaces. However, any suitable mechanism may be used to form those surfaces and to provide communication between those surfaces. According to some embodiments, as illustrated in FIGS. 6a and 6b, a penetrating medical device such as needle 500 contains a continuous balloon 600 which reaches both the distal tip 502 of the needle and a proximal end 510 of the needle. Continuous balloon 600 may be filled with a biocompatible fluid, for example, saline.

In use, a pressure is applied to proximal end 612 such that, while needle tip 502 is positioned within a high resistance matter 604, as shown in FIG. 6a, a distal end 606 of the balloon remains un-inflated or slightly inflated. However, the pressure on surface 612 is such that when needle tip 502 is advanced into a low resistance matter 608, as shown in FIG. 6b, distal end 606 of the balloon inflates. Inflation of the distal end 606 can be sensed at the proximal end, such as by a decreased fluid pressure at a compliant diaphragm 610 at a proximal end 612 of balloon 600. The decrease in fluid pressure at proximal end 612 of the balloon is significant enough for an operator to sense the change in pressure, or significant enough for a pressure sensor to detect the change. Alternatively or additionally, inflation of distal end 606 may result in a displacement of fluid sufficient to create a noticeable change in volume at the proximal end or be reflected in any other suitable way at an observable location.

Initial formation of balloon 600 may occur within needle 502, or balloon 600 may be manufactured outside of the needle and later inserted into the needle.

Figure 7:
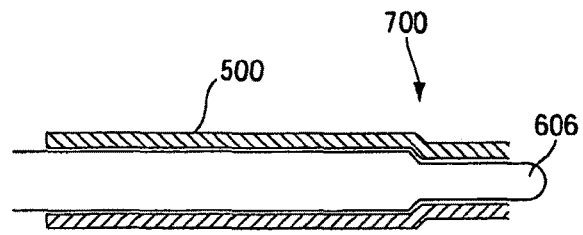
FIG. 7 illustrates a necked portion of a needle according to one embodiment of the invention.

As shown in FIG. 7, needle 500 and balloon 600 may include a necked section 700. The reduction in diameter at necked section 700 restricts the forward movement of balloon 600 to provide a limit on the distance balloon 600 can travel in the distal direction.

Figure 8:
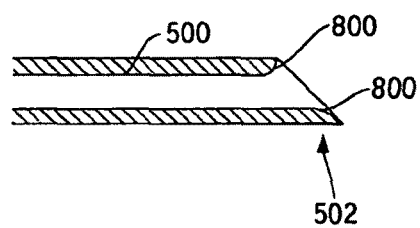
FIG. 8 illustrates a rounded needle tip, according to one embodiment of the invention.

As shown in FIG. 8, rounded inside edges 800 of needle tip 502 may be provided to help prevent puncturing of the balloon as it inflates and deflates.

Figure 9:
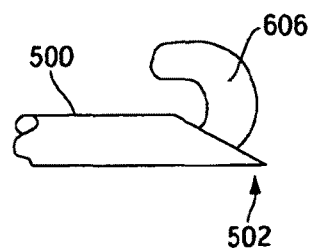
FIG. 9 illustrates an inflated balloon according to one embodiment of the invention.

The shape of balloon 600 as it inflates out of needle tip 502 need not be symmetric or spherical. In some embodiments, one of which is shown in FIG. 9, distal end 606 of balloon 600 inflates into a bent shape that takes it out of the direct path of portions of needle tip 502. In the embodiment illustrated, balloon 600 is shaped so that, as it inflates, it presses against a curved edge and expands away from a sharp edge.

Figure 10:
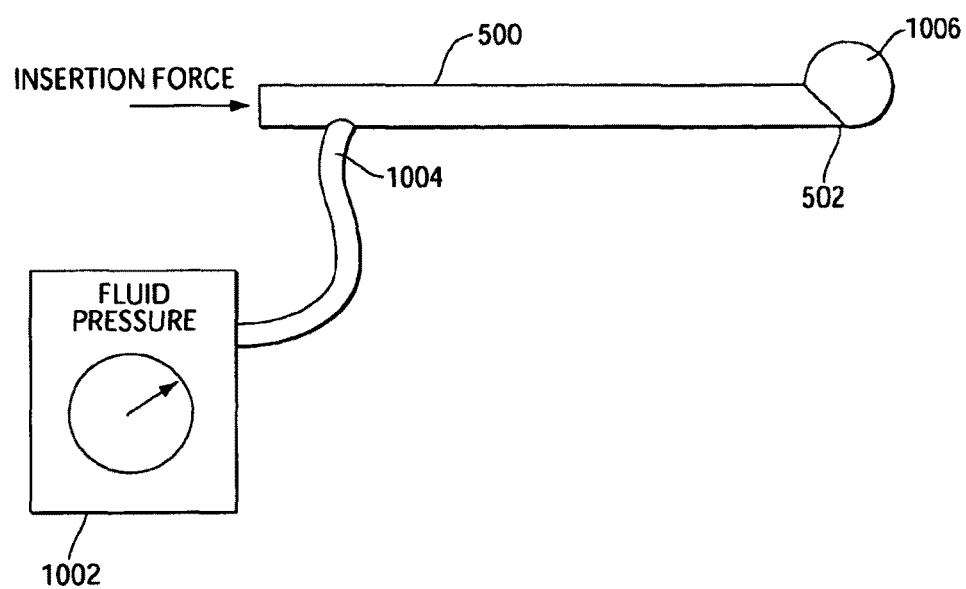
FIG. 10 illustrates a mechanical device applying pressure to a fluid within a penetrating medical device according to one embodiment of the invention.

It is not necessary that resistance at the tip of a penetrating device be sensed using a proximal membrane. In the embodiment illustrated in FIG. 10, needle 500 is coupled to a device 1002 which supplies a pressurized fluid 1004 to the needle. Needle 500 includes a membrane 1006 at the distal end of the needle. A pressure is applied to the fluid by device 1002 such that membrane 1006 either does not inflate or inflates an insignificant amount when needle tip 502 is positioned within a high resistance matter. When the needle tip is advanced into a low resistance matter with an operator's insertion force, a measurable pressure decrease may be sensed as membrane 1006 inflates. Device 1002 may be a pump box in some embodiments. Though, any suitable effect of membrane 1006 encountering a lower resistance may be sensed. Such effects may include sensing a flow of fluid as membrane 1006 expands or sensing the pressure required to maintain fluid within needle 500 in equilibrium.

In embodiments which include a continuous balloon within needle 500, device 1002 may be coupled to pressurized fluid within the balloon, and upon reaching low resistance matter, the expanding balloon results in a measurable pressure change.

Figure 11A:
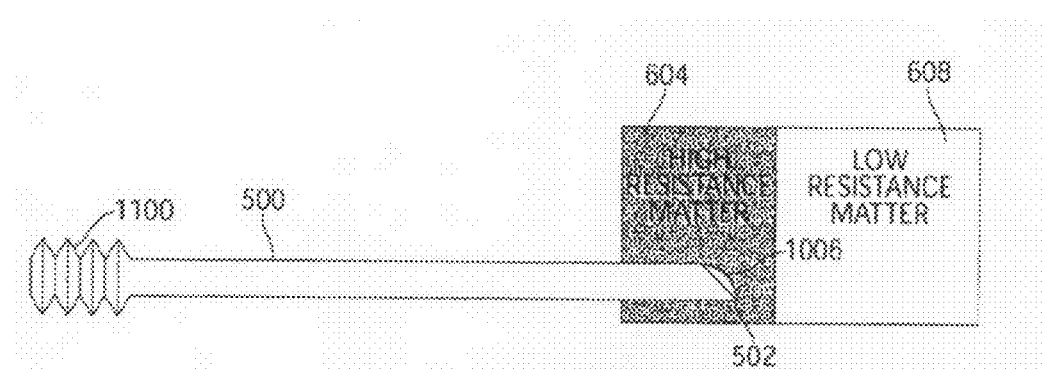
FIGS. 11a and 11b illustrate a penetrating medical device including bellows according to one embodiment of the invention.
Figure 11B:
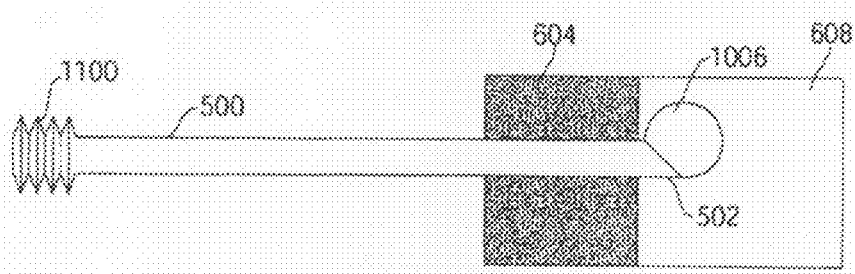

The ability to communicate an indication of a resistance at the tip of a device to a more proximal location may be used in ways other than to provide an indication of the location of the tip relative to low resistance spaces. The ability to communicate a force may be used to also control a driving force coupled to the penetrating device so that a driving force is coupled to the penetrating device as it encounters high resistance materials but the driving force is removed when the tip is positioned in a target space, such as in a lumen, such as a vein or artery a spinal column or other low resistance tissue or structure. In the embodiment illustrated in FIGS. 11a and 11b, bellows 1100 are attached directly to needle 500. Needle 502 and bellows 1100 contain a fluid, which may be a biocompatible fluid such as saline. When needle tip 502 is positioned within high resistance matter 604, bellows 1100 remain pressurized because membrane 1006 inflates insignificantly or not at all. Even as bellows 1100 are pushed by the operator to advance the needle, the bellows remain pressurized because less force is needed to advance the needle than to inflate membrane 1006 when advancing the needle tip through the high resistance matter. Once needle tip 502 reaches low resistance matter 608, however, the force needed to advance the needle is higher than the force that results in inflating membrane 1006. As a result, further pushing the bellows results in compression of the bellows and inflation of the membrane with the biocompatible fluid.

In some embodiments, resistance encountered at the tip of a device may be used to control a clutch mechanism to create an apparatus that provides a driving force to a penetrating medical device when the apparatus tip encounters material of high resistance, and when the apparatus tip encounters a low resistance material, no further driving force is applied to the apparatus. Such an apparatus may be used to stop advancing the tip of a device upon reaching a desired low resistance area, regardless of whether the operator continues to apply force to certain components.

Figure 12A:
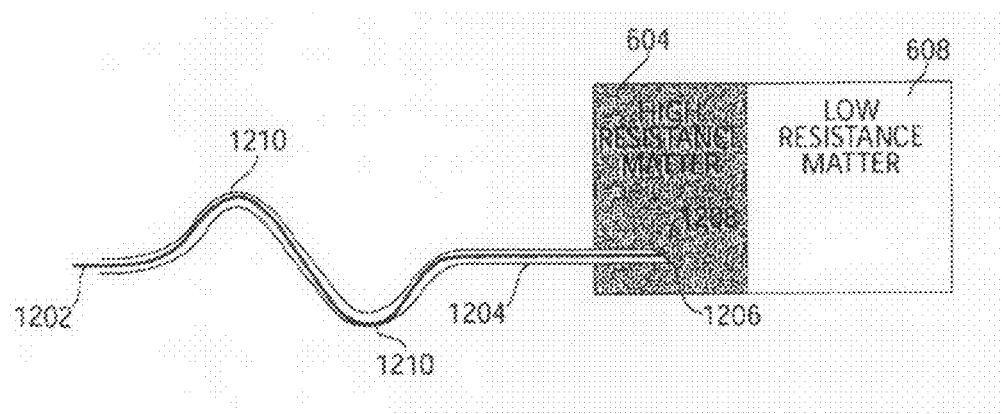
FIGS. 12a and 12b illustrate a penetrating medical device according to one embodiment of the invention.
Figure 12B:
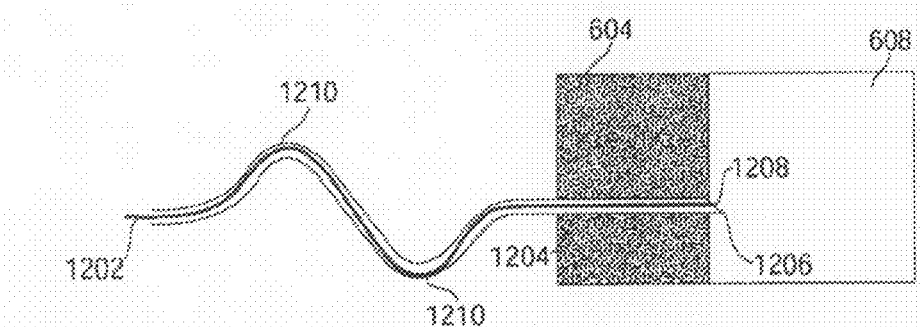

In the embodiment illustrated in FIGS. 12a and 12b, a catheter core 1202 is positioned within a curved needle 1204. A distal tip 1206 of needle 1202 is partially inserted into a high resistance matter 604 by pushing on the needle. After the needle has been partially inserted, continued advancement of the needle is provided by pushing on catheter core 1202. Catheter core 1202 does not exit through needle tip 1206 because the high resistance matter present at needle tip 1206 prevents a tip 1208 of the catheter core (which may be a blunt tip) from advancing into the matter. At a certain level of force, catheter core 1202 buckles, and catheter core 1202 contacts the interior of curved walls 1210 of needle 1204.

In the embodiment illustrated, the curved walls act like a capstan to wedge the catheter core in place. With the catheter core wedged, further forces applied to the catheter core are transferred to the needle wall, and the needle advances further through the high resistance matter. When the needle is advanced into a region of low resistance matter, the force resisting the catheter core tip decreases and the catheter core moves through the needle and into the low resistance matter. Allowed to move into the low resistance matter, the catheter core no longer buckles, no longer transfers significant force to the needle wall, and thus advancement of the needle no longer occurs. In this manner, the catheter inside the curved needle acts like a linear force clutch. For purposes herein, a catheter core, or any other suitable element used in a similar manner, is considered to be a member with a structural surface.

In some embodiments, needle 1204 may be formed of 17 Gauge thin-walled stainless steel tubing (0.058" O.D. and 0.048" I.D.), but may be formed of any suitable material and have any suitable size. Needle 1204 may include any suitable bend radii, but in some embodiments, bend radii of greater than 0.5" are used.

Catheter core 1202 may be any suitable material that is sufficiently pliable to buckle at forces above those encountered as it passes through a material deemed "low resistance," sufficiently rigid to transmit a force when buckled and sufficiently springy to disengage from the walls of needle 1204. Examples of suitable materials includes PTFE, PEEK, Nylon, Nitinol, or any metal or other material conventionally used to make catheter guide wires. In some embodiments, catheter core 1202 may have a diameter of less than 0.040 inches.

In one specific example of a method of using such an apparatus, a needle is partially inserted into the ligamentum flavum by pushing on the needle, and then further advancement is controlled by pushing on the catheter core. While the needle tip is positioned in the ligamentum flavum, pushing on the catheter core buckles the catheter, thereby pushing the needle further into the ligamentum flavum. Once the needle advances into the epidural space, the catheter core no longer buckles, and no further advancement of the needle occurs.

While the curved needle embodiment described above is described as including a catheter core, other suitable force-providing elements may be used. For example, in some embodiments, a flexible wire may be used within the needle to advance the needle through tissue. In still other embodiments, a force-providing element may be implemented on the outside of the needle.

Figure 12C:
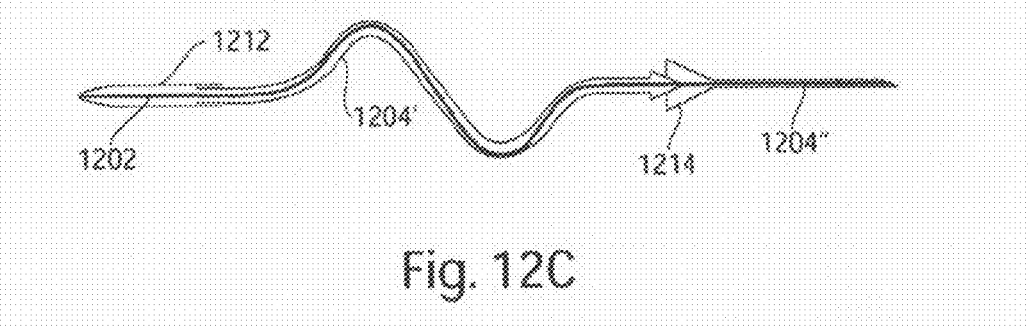
FIG. 12c illustrates a penetrating medical device according to a further embodiment of the invention.

As illustrated in FIG. 12c, instead of a one-piece needle, one embodiment of which is shown in FIGS. 12a and 12b, a curved section, such as an S-shaped section 1204' for example, and a straight section 1204" may be separable from one another. A Luer-Lok® connector 1214 or other suitable connector may used to permit selective connection of S-shaped section 1204' and straight section 1204". In some embodiments, S-shaped section 1204' and straight section 1204" may be configured to be separable without the use of a connector.

Straight section 1204" may be a standard needle in some embodiments. When straight section 1204" advances to the low resistance material, S-shaped section 1204' may be separated from straight section 1204" and catheter core 1202 may be removed. A catheter (not shown) then may be inserted through straight section 1204". In some embodiments, catheter core 1202 may be left in place when S-shaped section 1204' is removed, and a catheter may be slid over catheter core 1202 and into the low resistance material.

Figure 13A:
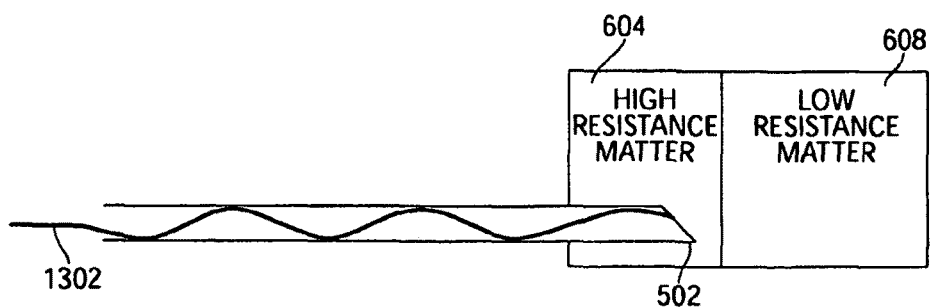
FIGS. 13a and 13b illustrate an alternative embodiment of a penetrating medical device.
Figure 13B:
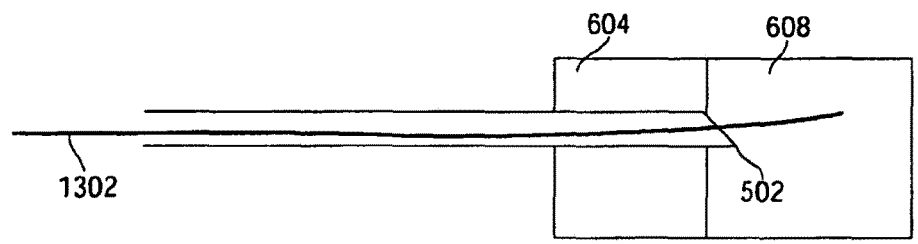

As shown in FIG. 12c, a hand piece 1212 may be included on the penetrating medical device, for example at the proximal end, to provide a grip area for the operator. In some embodiments, hand piece 1212 is a tube In another embodiment, a straight needle is used with a force-providing element to provide a linear force clutch. As illustrated in FIG. 13a, when needle tip 502 is positioned within high resistance matter 604, a force-providing element, such as flexible wire 1302, buckles and contacts the interior of the needle walls. Friction with the needle walls transfers the force on the flexible wire to the needle. When needle tip 502 enters low resistance matter 608, as shown in FIG. 13b, flexible wire 1302 no longer buckles and it is released from substantial contact with the needle. The flexible wire is then free to advance without pushing the needle further into the low resistance matter 608.

Figure 13C:
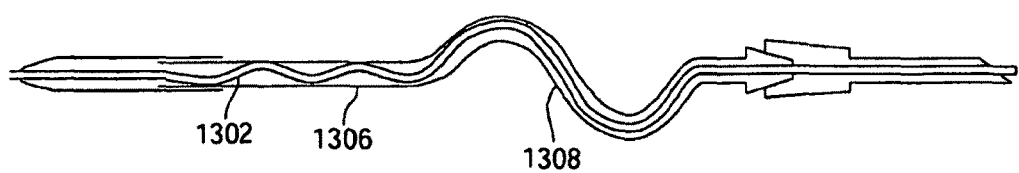
FIG. 13c illustrates an alternative embodiment of a penetrating medical device.

In some embodiments, one example of which is illustrated in FIG. 13c, the medical device may include serpentine portions in both the needle and the wire. As illustrated in FIG. 13c, a removable portion of the penetrating medical device may include both a straight section 1306 and an S-shaped section 1308. Flexible wire 1302 (or other suitable catheter core) may buckle within straight section 1306, and thereby contact the interior walls of straight section 1306. Additionally, the curved walls of S-shaped section 1308 act like a capstan to wedge the flexible wire in place. In some embodiments, the flexible wire (or other suitable catheter core) also may buckle within portions of S-shaped section 1308.

For embodiments of the penetrating medical device which include both a straight section and a curved section (e.g., an S-shaped section), a mathematical model has been created to estimate the output force of the catheter core (e.g., a flexible wire) as a function of the axial input force on the catheter core. Equation (1) presented below was developed by modeling the amount of force absorbed by the curved and straight sections of the device, and then subtracting the estimated forces from the input force. By conducting test measurements, a correction factor has been incorporated into the equation.

The force for the straight section uses the helical buckling equation while the force for the curved section is for the unbuckled state. For the model, it is assumed that the catheter core is always helically buckling in the straight section while not buckled in the curved section. The force output by the catheter core is modeled to be:

$$F_{out\,predicted} = F_{in} - (\mu L_{curved} F_{in}/R + 10\mu D_{core} F_{in}^2 r/(EI)) \quad (1)$$

where $\mu$ is the coefficient of friction between the catheter core and the interior wall, $L_{curved}$ is the length of the interior of the curved section (m) that the catheter core is touching, $F_{in}$ is the input force (N) applied at the hand piece, $D_{core}$ is the diameter of the catheter core (m), R is the average radius of the curves in the curved section (m), r is the radial gap spacing between the catheter core and the interior wall (r), E is the modulus of elasticity (N/m$^2$) of the catheter core, and I is the moment of inertia of the catheter core (m$^4$).

The embodiments of FIGS. 12a, 12b, 12c, 13a, 13b, and 13c provide examples of apparatus including a force translating member that translates an axial force, generated by resistance encountered at the tip of a medical device, to a transverse force, such as a radial force. Such force translation allows a driving member, such as a catheter core, to selectively engage a needle based on resistance encountered. Other suitable elements may be used to create a "clutch" to selectively drive a penetrating medical device.

Figure 14A:
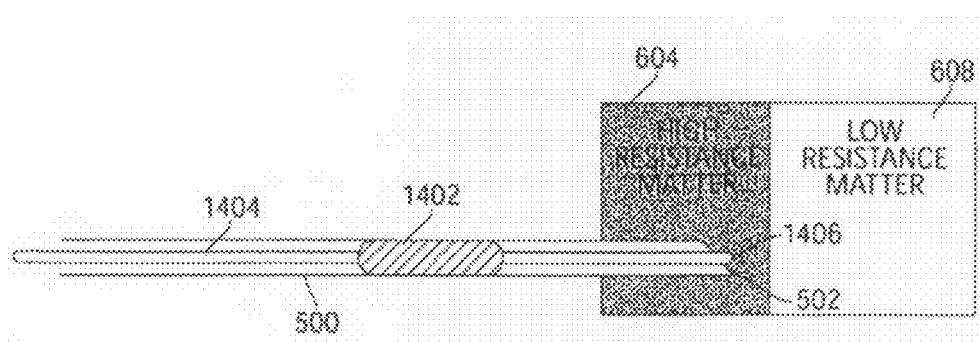
FIGS. 14a and 14b illustrate a penetrating medical device which includes a high Poisson ratio material according to one embodiment of the invention.
Figure 14B:
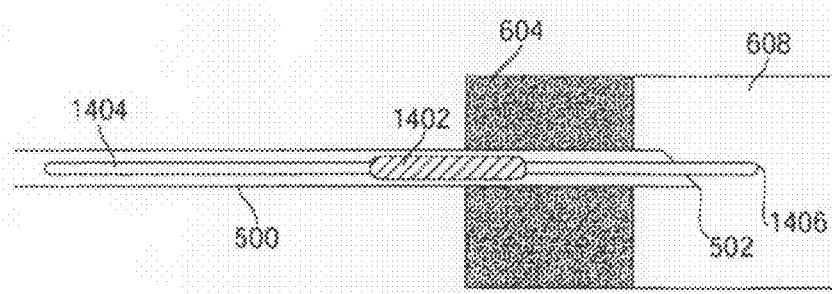

Another type of suitable element is illustrated in FIGS. 14a and 14b. A material or device having a high Poisson ratio (hereinafter, "Poisson element") may be used as part of an apparatus which provides a linear force clutch for controlling advancement of a penetrating medical device. In some embodiments, the Poisson element may be a balloon or an elastomer. In the embodiment illustrated in FIGS. 14a and 14b, an element 1402 including high Poisson ratio material acting as a Poisson element is coupled to a force-providing core 1404. When the core is pushed with needle tip 502 positioned in high resistance matter 604 such that a distal end 1406 of core 1404 cannot substantially exit needle tip 502, Poisson element 1402 is compressed and expands radially. Once sufficiently expanded, the Poisson element contacts the interior walls of needle 500, and the operator's compressive force on core 1404 is transferred to the needle walls, thereby advancing the needle. Once the needle tip advances into low resistance matter 608, distal end 1406 of core 1404 advances through the low resistance matter, the compressive force on the Poisson element decreases, and the Poisson element no longer significantly contacts the needle walls. In this manner, further pushing on core 1404 does not further advance needle 500.

Figure 15:
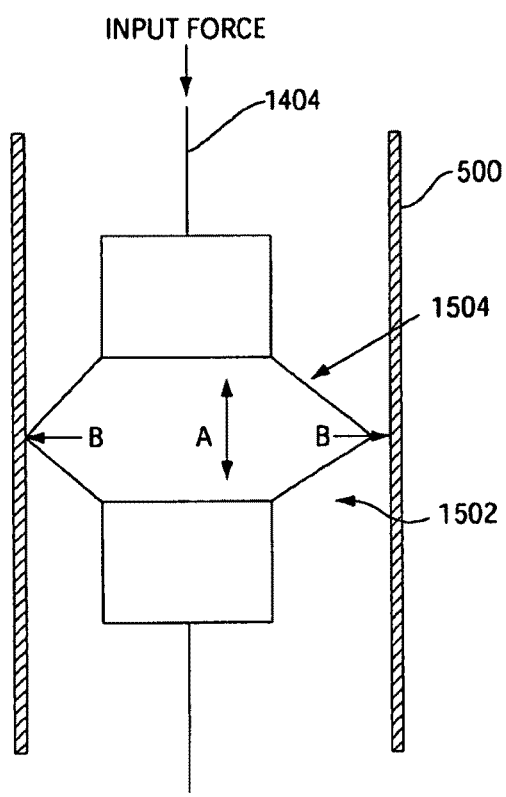
FIG. 15 illustrates a penetrating medical device including a mechanical expansion spring according to one embodiment of the invention.

As an example of another embodiment of a Poisson element, a mechanical expansion spring may be used to selectively transmit force from a core to the needle walls. As shown in FIG. 15, a mechanical expansion spring 1502 includes two flexible spring members 1504 which are displaced radially when a compressive axial force is applied via core 1404. With sufficient axial force, flexible spring members 1504 contact the interior needle walls and the friction transfers the force of the core 1404 to needle 500. The mechanical expansion spring is configured to expand sufficiently radially (direction B) when the resistance of expected high resistance matter is encountered by the distal end of core 1404 as needle 500 is being advanced through the high resistance matter. When the needle tip advances into expected low resistance matter, the core is free to extend out of the needle, allowing the expansion spring to elongate in the axial direction (direction A) and retract in the radial direction, thereby ending its contact with the needle walls. Accordingly, further advancement of the needle does not occur within the low resistance matter. While the embodiment illustrated in FIG. 15 includes two flexible spring members, three, four, or more than four flexible spring members may be included in some embodiments.

Figure 16A:
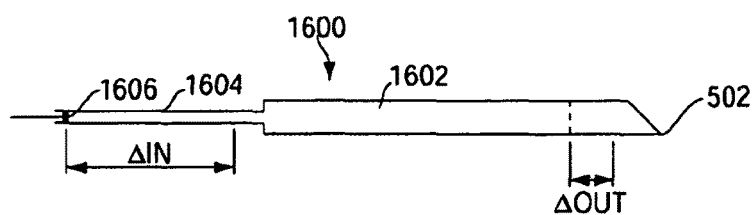
FIGS. 16a and 16b illustrate a sensitivity amplifier according to one embodiment of the invention.
Figure 16B:
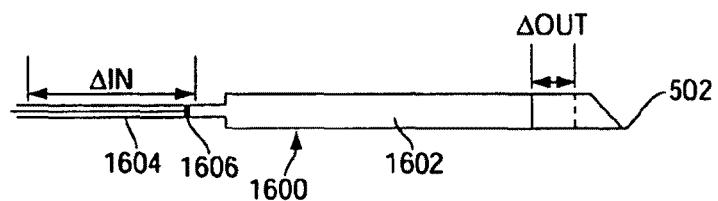

A sensitivity amplifier may be employed in some embodiments to amplify the effect of a change in resistance encountered at the tip of a penetrating medical device. Such amplification may improve the reliability with which a clutch engages or help an operator observe changes in the material through which the needle tip is advancing. For example, as illustrated in FIGS. 16a and 16b, a needle 1600 may have a distal section 1602 with a first diameter and a proximal section 1604 with a second, smaller diameter. As a piston 1606 is pushed into proximal section 1604, a release of biocompatible fluid from the distal section that is equal to the volume of fluid occupying a longitudinal length of tout will permit piston 1606 to move a longer, longitudinal length of Δin because the cross-sectional area of proximal portion 1604 is less than the cross-sectional area of distal section 1602. This embodiment of a sensitivity amplifier may be used with a needle having no membrane at needle tip 502, or it may be used with a needle that has a membrane at the needle tip (similar to the embodiment illustrated in FIGS. 11a and 11b). A sensitivity amplifier may be used with other embodiments described herein, and other suitable sensitivity amplifiers may be used to aid with the sensing of needle advancement.

An operator may prefer to retain an open channel within the penetrating medical apparatus. For example, in some cases, the operator may desire to observe fluid flowing from the body to help determine the location of the needle tip. In some cases, the operator may wish to inject fluid into the region in which the needle tip is placed. To accommodate fluid flow through the needle, various embodiments of needle and/or core arrangements may be put to use.

Figure 17A:
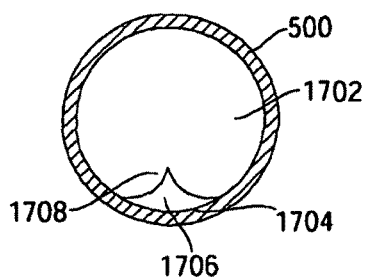
FIGS. 17a-17d illustrate various embodiments of penetrating medical devices including one or more longitudinal channels.

For example, as shown in FIG. 17a, core 1702 may have a diameter that contacts or almost contacts an interior surface 1704 of the needle walls around most of the perimeter of the core. In one or more areas, however, a space 1706 may be formed between core 1702 and interior surface 1704 with a section 1708 of the core that has a smaller radius. The space 1706 forms a longitudinal channel through which fluid may flow.

Figure 17B:
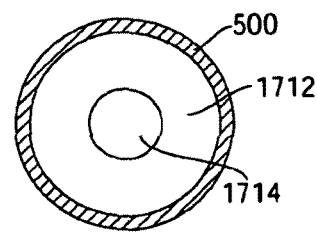

A hollow core 1712 may be used in some embodiments to provide a channel, as illustrated in FIG. 17b. The core 1712 reaches or nearly reaches the interior surface of the needle around the entire perimeter of the core, but a channel 1714 is provided through the interior of the core.

Figure 17C:
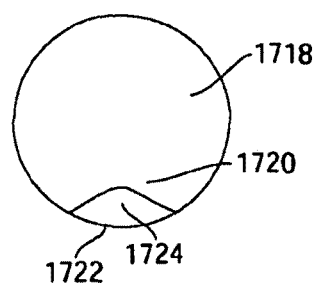

In another embodiment, as illustrated in FIG. 17c, a substantially solid needle 1718 may be used as a penetrating device, and a portion 1720 of the solid material may have a reduced radius. A needle wall 1722 forms a flow space 1724 in conjunction with reduced radius portion 1720 of the solid needle.

Figure 17D:
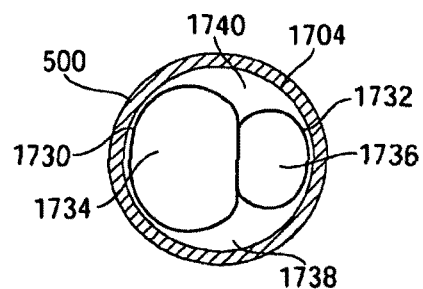

In still a further embodiment of a channel within a penetrating medical device, a flow channel may be formed within the area between the needle wall and the outside of a core, and also within a hollow core (or cores). For example, as illustrated in FIG. 17d, two hollow cores 1730 and 1732 may form two channels 1734 and 1736. Additional channels 1738 and 1740 may be formed between the exterior of the cores 1730, 1732 and the interior surface 1704 of needle 500. In this manner, multiple channels may be formed for fluid feedback, fluid injection, or any other suitable purpose.

A multi-channel device may be configured to allow fluid flow in one or more channels, and the presence of a core and/or Poisson element in another channel. In this manner, separated channels may be used for different purposes. In some embodiments, a first channel may be used for holding pressurized fluid to be used as part of a sensing arrangement, and a second channel may be used to deliver fluid to the body.

Figure 18:
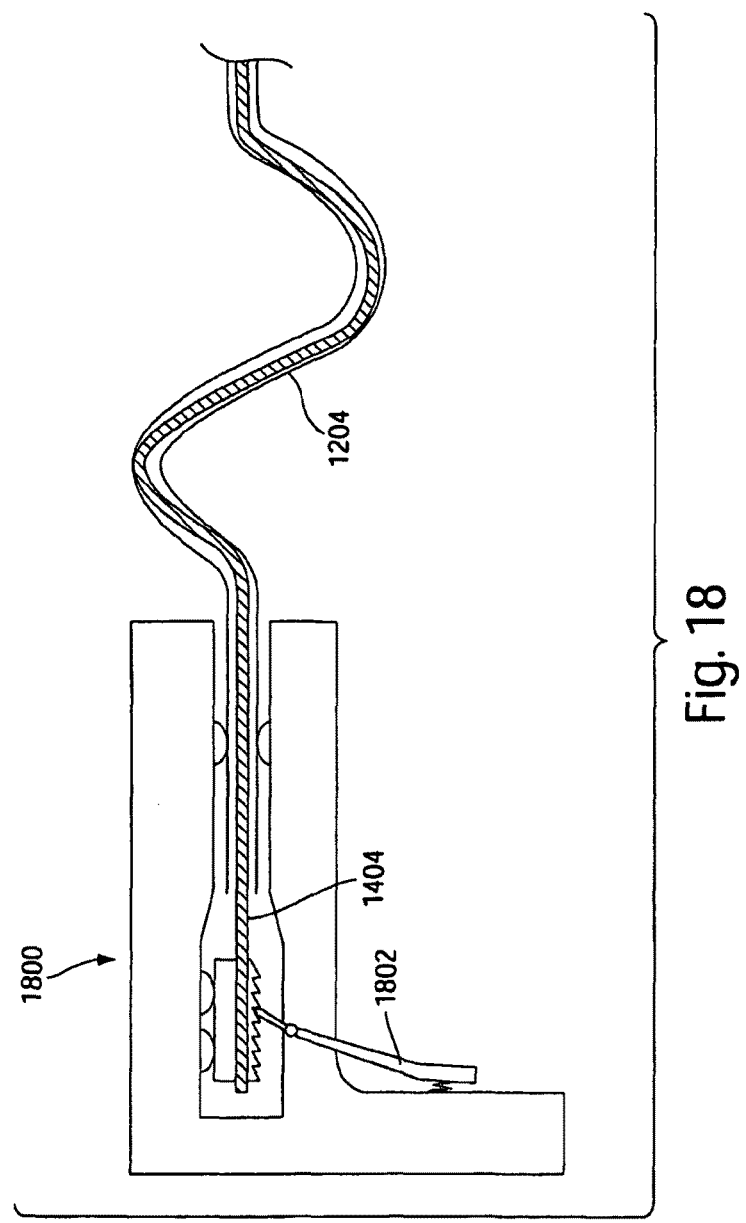
FIG. 18 illustrates a device for providing step-wise advancement of a penetrating medical device according to one embodiment of the invention.

The penetrating medical devices described herein may further employ an advancing arrangement which limits the advancement of a core such as a catheter core, a flexible wire, etc., even when low resistance matter is encountered. For example, as illustrated in FIG. 18, a device 1800 with a trigger handle 1802 may be used to push on core 1404. Each complete pull of trigger handle 1802 advances core 1404 out of device 1800 by a certain distance. When core 1404 is wedged in curved needle 1204, needle 1204 advances by the same distance. Once the needle tip reaches matter with a low resistance, the core advances in a step-wise manner into the low resistance matter, such that each discrete motion of the operator advances the core at most by the distance provided by one complete pull of the handle. In this manner, unintentional advancement of core 1404 into low resistance matter can be limited. Device 1800 is shown by way of example only, and other suitable devices and methods may be used to limit the advancement of core 1404 upon encountering a low resistance material, such as by limiting advancement to a discrete distance.

Figure 19A:
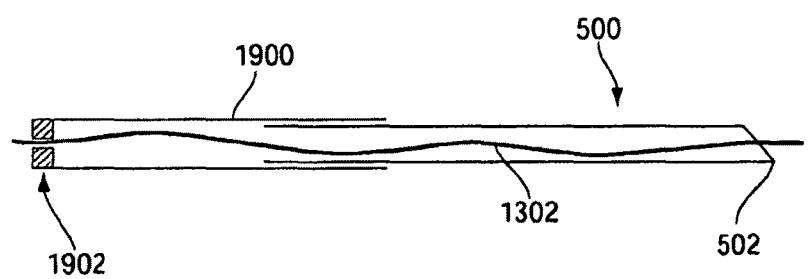
FIGS. 19a and 19b illustrate embodiments of a device for providing advancement of a penetrating medical device according to embodiments of the invention.
Figure 19B:
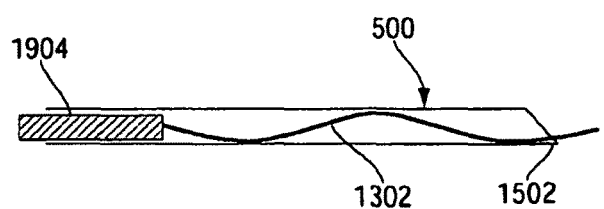

Another embodiment of an advancing arrangement for use with penetrating medical devices described herein is illustrated in FIG. 19a. A grip tube 1900 holds flexible wire 1302 at a grip location 1902. Grip tube 1900 has a diameter that is slightly larger than straight needle 500 such that grip tube 1900 may be translated axially relative to needle 500. Grip tube 1900 provides off axis stability to one or both of the needle and the flexible wire. In an alternative embodiment, as illustrated in FIG. 19b, a rigid rod 1904 may be used to apply force to flexible wire 1302. As with various embodiments disclosed herein, when needle tip 502 is positioned within high resistance matter, a force-providing element, such as flexible wire 1302, buckles and contacts the interior of the needle walls. Friction with the needle walls transfers the force on the flexible wire to the needle. When needle tip 502 enters low resistance matter, flexible wire 1302 no longer buckles and it is released from substantial contact with the needle. The flexible wire is then free to advance without pushing the needle further into the low resistance matter. Either of the advancing arrangements illustrated in FIGS. 19a and 19b may be used as a stand-alone device, or may be used in combination with other components, such as a step-wise advancing device similar to the embodiment illustrated in FIG. 18. In some embodiments, grip tube 1900 may be sized and configured to translate axially along the interior of needle 500.

Figure 20A:
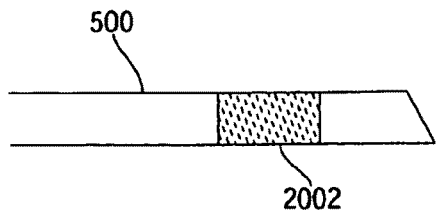
FIGS. 20a-20d illustrate embodiments of a penetrating medical device having an increased resistance between the penetrating portion and surrounding material according to embodiments of the invention.
Figure 20B:
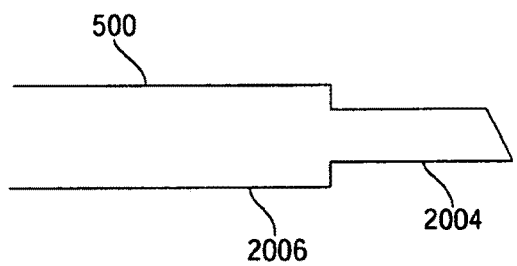
Figure 20C:
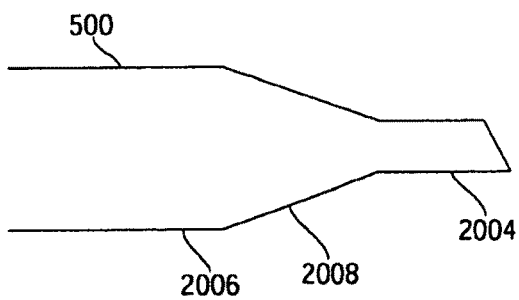
Figure 20D:
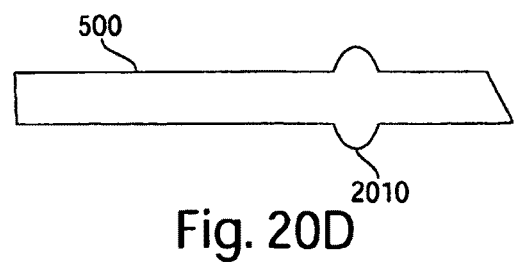

When using various embodiments disclosed herein, sufficient resistance may not exist between the penetrating medical device and the surrounding material to stop advancement of the penetrating medical device when it reaches low resistance material. In various embodiments disclosed herein, the needle may include one or more features that increase the resistance between the needle and the surrounding material. For example, as shown in the side view of FIG. 20a, an outer surface of needle 500 may include an area of surface roughness 2002 that is higher than a standard needle. As illustrated in the cross-sectional view of FIG. 20b, needle 500 may have a first section 2004 with a first outer diameter and a second section 2006 having a larger outer diameter than first section 2004. The change in diameter creates an increased resistance to advancement. The cross-sectional view of FIG. 20c shows needle 500 having first section 2004 with a first outer diameter and second section 2006 having a larger outer diameter than first section 2004, and additionally includes a transition section 2008 between first section 2004 and second section 2006. In an alternative embodiment, needle 500 may include a very short or non-existent first section 2004, such that transition section 2008 is positioned close to or at the distal tip of needle 500. FIG. 20d shows a cross-sectional view of a needle 500 having a curved bump 2010 that extends around the circumference of the needle. In an alternative embodiment, a toroidal-shaped component may be positioned around the circumference of the needle. In another embodiment, a semi-spherical bump may be included at one or more distinct positions on the needle.

The particular arrangements and sizes of any features that increase resistance with surrounding material may be based on the type of material being penetrated and the type of space being targeted.

Figure 21:
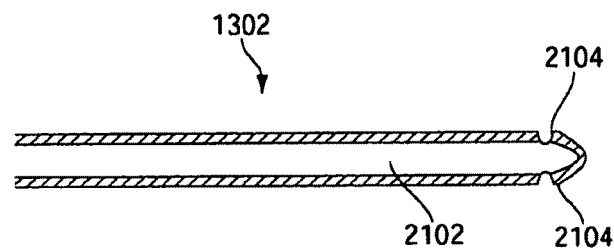
FIG. 21 illustrates a flexible wire according to one embodiment of the invention.

One embodiment of a catheter core, such as flexible wire 1302 for example, is shown in a cross-sectional view in FIG. 21. In this embodiment, flexible wire 1302 has a lumen 2102 and one or more passages 2104 that lead to lumen 2102 through the wall of flexible wire 1302. Lumen 1302 may be used for insufflation, drug delivery, or drainage of excess bodily fluids in some embodiments. Lumen may be used to inject fluid when a target region is reached by the penetrating medical device. The injection of fluid may be provided by using bellows. In some embodiments, a balloon may be provided within the lumen of flexible wire 1302, and the balloon may be filled with a fluid to provide pressure feedback to the operator.

In various embodiments described above, a membrane is provided at a needle tip. In some embodiments, needle tip may be left open and optionally may have a restricted diameter opening. In such embodiments, fluid at the opening may not have a structural surface, but high resistance matter nonetheless may prevent biocompatible fluid from exiting the needle tip, while low resistance matter may allow the fluid to flow from the needle tip. Similar to the inflation of a membrane in low resistance matter, the initiation of flow from the needle tip decreases the pressure sensed by the operator, indicating advancement into low resistance matter.

In embodiments which include a membrane or balloon at the needle tip, in addition to providing an indication of reaching low resistance matter, inflation of the membrane or balloon may serve to prevent or reduce further advancement of the needle tip into low resistance matter. For example, an inflated membrane or balloon may block the sharp edge of the needle and/or present a large surface area which cannot be advanced through the low resistance matter.

Also, an embodiment was described in which a catheter core was used as a driving element. There is no requirement that the driving element be at the center of a catheter. FIGS. 17a-17d illustrate various multi-lumen devices and the driving element may be configured in any of suitable lumen or otherwise constrained in a desired position.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

The invention claimed is:

1. A device adapted to penetrate a body, the device comprising:
    at least one first member having a distal tip and a lumen having an opening adjacent the distal tip; and
    a second member disposed within the lumen, the second member having a structural surface exposed through the opening, and the second member being adapted to have a first state in response to a first pressure on the surface, and a second state in response to a second pressure on the surface in which force applied in the distal direction on the second member advances the distal tip of the first member in the distal direction.

2. The device of claim 1, wherein the second member is constructed and arranged to move relative to the first member in the second state and to engage the first member in the first state.

3. The device of claim 2, wherein the lumen has an interior surface and the second member is adapted to frictionally engage the interior surface when in the first state.

4. The device of claim 1, wherein the second member comprises a fluid filled membrane and the structural surface is within the lumen in the first state and outside the lumen in the second state.

5. The device of claim 1, wherein the first member is elongated along an axis and the second member comprises an elongated member, a portion of the elongated member having a first dimension in a direction perpendicular to the axis when in the first state, and the portion of the elongated member having a second dimension, less than the first dimension, when in the second state.

6. A method of operating a device adapted to penetrate a body, the device comprising at least one first member having a distal tip and a lumen having an opening adjacent the distal tip and a second member disposed within the lumen, the second member having a surface exposed through the opening, the method comprising:
    advancing the device through a first region of the body by applying a force to the second member, the first region providing a first resistance to penetration of the device, wherein the second member has a first configuration in response to a first pressure on the surface created by the first resistance; and
    advancing the device into a second region of the body, the second region providing a second resistance to penetration of the device, wherein the second member has a second configuration and disengages from the first member in response to the second pressure on the surface created by the second resistance.

7. The method of claim 6, wherein applying a force to the second member results in placing, from within the lumen, a pressure on the surface, the pressure being less than the first pressure and more than the second pressure.

8. The method of claim 7, further comprising sensing that the configuration of the second member has changed from the first configuration to the second configuration.

9. The method of claim 8, wherein the second member comprises an expandable membrane, and wherein sensing that the configuration of the second member has changed from the first configuration to the second configuration comprises sensing an increased resistance to advancing the device because the membrane has expanded into the body.

10. A medical device adapted to penetrate a body, the device comprising:
    a first element having a distal tip and a lumen having an opening; and a force-providing element disposed in the lumen, the force-providing element being configured to receive an applied force and selectively transfer at least a portion of the applied force to the first element to advance the device within the body, based at least in part on the resistance of the matter which the force-providing element contacts at the opening; wherein the medical device is constructed and arranged such that with the opening positioned within a matter having a first resistance to advancement of the force-providing element, the force-providing element transfers a first portion of the applied force to the first element, and with the opening positioned within a matter having a second resistance that is lower than the first resistance, the force-providing element transfers either no force or less of the applied force to the first element as compared to the first portion.

11. The medical device as in claim 10, wherein the second portion of the applied force is insufficient to advance the first element.

12. The medical device as in claim 10, wherein the force-providing element comprises a core element that is constructed and arranged to buckle and contact the first element when the core encounters matter having the first resistance and to be longitudinally movable relative to the penetrating medical device when the core element encounters matter having the second resistance.

13. The medical device as in claim 12, wherein the first element comprises a serpentine lumen.

* * * * *